(12) United States Patent
Williams et al.

(10) Patent No.: US 10,765,770 B2
(45) Date of Patent: Sep. 8, 2020

(54) HALOGENATED HETEROCYCLIC N-HALAMINE COATED GARBAGE BAGS

(71) Applicant: The Glad Products Company, Oakland, CA (US)

(72) Inventors: Jeffrey F. Williams, Langley, WA (US); Simon Johnston, Bellevue, WA (US)

(73) Assignee: THE GLAD PRODUCTS COMPANY, Oakland, CA (US)

(*) Notice: Subject to any disclaimer, the term of this patent is extended or adjusted under 35 U.S.C. 154(b) by 0 days.

(21) Appl. No.: 16/380,626

(22) Filed: Apr. 10, 2019

(65) Prior Publication Data
US 2019/0231916 A1    Aug. 1, 2019

Related U.S. Application Data

(62) Division of application No. 15/872,617, filed on Jan. 16, 2018, now Pat. No. 10,512,705.
(Continued)

(51) Int. Cl.
*A61L 9/012*    (2006.01)
*A61L 2/18*    (2006.01)
(Continued)

(52) U.S. Cl.
CPC .............. *A61L 9/012* (2013.01); *A01N 25/34* (2013.01); *A01N 59/00* (2013.01); *A61L 2/18* (2013.01); *A61L 2/232* (2013.01); *A61L 9/042* (2013.01); *A61L 9/046* (2013.01); *C07D 233/76* (2013.01); *C07D 233/82* (2013.01); *C08J 7/065* (2013.01); *A61L 2202/23* (2013.01); *A61L 2209/20* (2013.01); *A61L 2209/21* (2013.01); *C08J 2323/06* (2013.01)

(58) Field of Classification Search
CPC .......... A61L 9/012; A61L 9/046; A61L 9/042; A61L 2/232; A61L 2/18; A61L 2209/21; A61L 2209/20; A01N 25/34; C07D 233/176; C07D 233/82; C08J 7/065; C08J 2323/06; B01D 2257/93; B01D 2257/90; B01D 2251/18; B01D 53/78; C02F 2303/02; C02F 2303/76
See application file for complete search history.

(56) References Cited

U.S. PATENT DOCUMENTS 6,162,452 A * 12/2000 Worley .................. A01N 43/76
                                                                   424/405
10,512,705 B2 * 12/2019 Williams ................ A61L 9/012

* cited by examiner

*Primary Examiner* — Carlos A Azpuru
(74) *Attorney, Agent, or Firm* — Thomas C. Feix (57) ABSTRACT

Articles can be provided with odor resistance by applying a dispersion of a halogenated heterocyclic N-halamine in an inert liquid carrier onto the surface of the article and allowing the inert liquid carrier to penetrate into it. The N-halamine accordingly becomes deposited on the surface of the article after the inert liquid carrier penetrates into the article. This method can be used to provide odor resistance to a variety of substrates, including garbage bags. It can also be used to deposit other functional particulates onto the surface of substrates having sufficient porosity to take up the vehicle. For instance, such functional particles can be oxidants that display antimicrobial and/or enzyme inhibitory efficacy or particles having toxin interaction potentials through oxidative degradation or adsorption of toxic substances in air and/or water, such as fluoride uptake by metal oxide microparticles.

19 Claims, 4 Drawing Sheets

Related U.S. Application Data (60) Provisional application No. 62/447,187, filed on Jan. 17, 2017.

(51) Int. Cl.
*C07D 233/82* (2006.01)
*C08J 7/06* (2006.01)
*C07D 233/76* (2006.01)
*A01N 25/34* (2006.01)
*A01N 59/00* (2006.01)
*A61L 2/232* (2006.01)
*A61L 9/04* (2006.01)

HALOGENATED HETEROCYCLIC N-HALAMINE COATED GARBAGE BAGS

This is a divisional application of U.S. patent application Ser. No. 15/872,617, filed on Jan. 16, 2018, which claims the benefit of U.S. Provisional Patent Application Ser. No. 62/447,187, filed on Jan. 17, 2017. The teachings of U.S. patent application Ser. No. 15/872,617 and U.S. Provisional Patent Application Ser. No. 62/447,187 are incorporated herein by reference in their entirety.

TECHNICAL FIELD OF THE INVENTION

The present invention relates to compositions that can be used to prevent and eliminate odors which are emitted from solid articles and aqueous media. It also provides methods for utilizing such compositions in specific applications. In one embodiment of this invention novel compositions are used remove contaminants, including toxic materials, from aqueous media or air. In another embodiment the novel compositions are used to inhibit enzymes. In another embodiment the novel compositions are used to inactivate microbes.

BACKGROUND OF THE INVENTION

It is desirable to eliminate or at least to control odors that result from various activities and/or which are associated with certain objects and places. For instance, the repugnant odor that is sometimes experienced in public restrooms can be almost overwhelming. Portable toilets also commonly emit malodors. Garbage cans, dumpsters, trash bags, dirty clothes hampers, and a wide variety of other articles used in homes, commercial settings and industry can also be the source of unpleasant odors.

Frequent and thorough cleaning is an age-old and generally effective way to control odors in many settings. The methodical cleaning of an article removes or destroys odor-causing bacteria and other materials that can be the source of odors. Over the years, excellent cleaning products and disinfectants, including soaps and detergents containing antimicrobial agents, have been developed. However, in some cases cleaning is not an effective or practical means for odor control.

In addition to cleaning products there are numerous commercially available compositions which can be used to control or reduce the level of various odors. These odor management compositions can be divided into three categories which are based on their functionality. These categories of odor management compositions are defined as odor masking compositions (which masks odors through the use of fragrances or perfumes), deodorizing/sanitizing compositions, which bind to odors or eliminate the microorganisms that are responsible for the production of said odors, and combination odor masking and deodorizing/sanitizing compositions (which bind to odors and eliminate the microorganisms responsible for the production of said odors, as well as introducing a perfume or fragrance). Odor masking compositions primarily function by providing a large quantity of a perfume or fragrance that overwhelms the senses, masking odors without removing or modifying the source of said odor. Deodorizing/sanitizing compositions function by containing active agents that function in a deodorizing and antimicrobial capacity. The deodorizing agents chemically bind to existing odors deactivating them, while the antimicrobial agents are responsible for eliminating the microorganisms responsible for the production of said odors. Combination odor masking and deodorizing/sanitizing compositions are provided with both a deodorizing/sanitizing agent and an odor masking composition that eliminates the source of a particular odor while providing an additional fragrance or perfume to the area of application. Of these odor management compositions, deodorizing/sanitizing compositions are of particular interest due to their various applications and incorporation into new and existing odor management systems.

Current deodorizing/sanitizing compositions can be formulated using a plurality of active deodorizing/sanitizing agents. One of these active sanitizing agents includes sodium tetraborate decahydrate, commonly known as "borax." Borax is a boron salt that has the chemical formula $Na_2[B_4O_5(OH)_4] \cdot 8H_2O$ in solution. Borax is able to function as a deodorizing/sanitizing agent as a result of its co-complexing ability that enables it to stably bind with various substances forming complex ions. The ability to form complex ions enables borax to function as a deodorizing agent but additionally grants it antimicrobial properties. These antimicrobial properties are a result of the borax formed complex ions inhibiting key metabolic pathways of several microorganisms.

Another active deodorizing/sanitizing agent is colloidal silver. Colloidal silver is metallic silver nanoparticles formed after ionization of silver or as a result of a chemical reaction which synthesize zero valent silver from mono valent silver cations. The zero valent silver cations that are formed, disperse in a colloidal suspension, wherein the colloidal suspension provides the silver nanoparticles separated between 10 nanometers (nm) to 100 nanometers (nm) apart from another silver nanoparticle. Through this unique arrangement, silver nanoparticles have unique optical, electrical and thermal properties, in part due to significant surface area to volume ratio. The colloidal dispersal of the silver nanoparticles grants a solution with silver nanoparticles with deodorizing and antimicrobial properties. The deodorizing properties are provided by the ability of the silver nanoparticles to react with substances more frequently due to the surface area to volume ratio. The antimicrobial properties are provided by the ability of the silver nanoparticles to inhibit aerobic metabolism in various microorganisms.

U.S. Pat. No. 9,392,784 provides an odor management composition and a method for creating said odor management composition containing the active deodorizing and antimicrobial agents of silver nanoparticles in a colloidal suspension, commonly known as colloidal silver, and sodium tetraborate decahydrate, commonly known as borax. The method of U.S. Pat. No. 9,392,784 creates a combination colloidal silver borax solution through an in situ reaction that occurs at standard temperature and pressure values, between a formulated borax solution and a formulated silver nanoparticle source solution. The resulting colloidal silver borax solution results in a deodorizing and antimicrobial solution that eliminates various odors and reduces microbial presence responsible for the production of said odors. Additionally, the colloidal silver borax solution is reported to have long-term shelf stability.

U.S. Pat. No. 9,392,784 more specifically reveals an odor eliminating solution comprises the active deodorizing and antimicrobial agents of silver nanoparticles dispersed in colloidal suspension in a solution containing excess sodium tetraborate decahydrate, commonly referred to as borax. The silver nanoparticles provide deodorizing and antimicrobial properties through the colloidal dispersion which provides a high surface area to volume ratio for the suspension. The sodium tetraborate decahydrate provides deodorizing and antimicrobial properties through its co-complexing ability with various substances. The combination of both is reported to provide long term stability as well as deodorizing and antimicrobial activity.

The problem associated with water which is contaminated with harmful materials is a serious problem which is of growing concern. For instance, water supplies can easily become contaminated with toxic compounds from industrial, commercial, mining, and agricultural sources. More specifically, in the world today water supplies from lakes, rivers, and underground sources are frequently contaminated with phosphates, chromates, arsenates, and a wide variety of dangerous organic compounds. In other cases, it is important to be capable of effectively removing toxic compounds which are intentionally introduced into bodies of water or the air by terrorist groups or in warfare. For example, the ability to effectively remove gases used in warfare, such as mustard gas or nerve gas, from air is of critical importance.

A technique for the purification of contaminated water is described in "Surface Engineered Zeolite: An Active Interface for Rapid Adsorptionand Degradation of Toxic Contaminants in Water" by Ruchi Shaw, Richa Sharma, Sangeeta Tiwari, and Sandeep Kumar Tiwari, ACS Appl. Mater. Interfaces 2016, 8, 12520-12527. In this method zeolite is surface modified to form novel multifunctional materials having capability for simultaneous and facile removal of heavy metals [Pb(II)], organic pollutants [methylene blue dye], and microorganisms [*E. Coli*, *S. Aureus*, and *Pseudomonas*] from contaminated water. The procedure involves formation of core-shell particles with a functional core of zeolite and a porous shell of ZnO nanoflakes which not only imparts photocatalytic and antibacterial properties but also renders the surface negatively charged, thereby facilitating rapid adsorption of Pb(II) and methylene blue dye. However, the procedure described in this publication is of questionable commercial applicability.

Free standing and strong odor-removing composite films of cellulose nanofibrils (CNF) with a high content of nanoporous zeolite adsorbents made by being colloidally processed are described in "Nanocellulose-Zeolite Composite Films for Odor Elimination" by Neda Keshavarzi, Farshid Mashayekhy Rad, Amber Mace, Farhan Ansari, Farid Akhtar, Ulrika Nilsson, Lars Berglund, and Lennart Bergstro, ACS Appl. Mater. Interfaces 2015, 7, 14254-14262. In this publication it is reported that thermogravimetric desorption analysis and infrared spectroscopy combined with computational simulations showed that commercially available silicalite-1 and ZSM-5 have a high affinity and uptake of volatile odors like ethanethiol and propanethiol. It is further reported that these materials are also effective in the presence of water.

SUMMARY OF THE INVENTION

This invention reveals a method of manufacturing an odor resistant article which comprises applying a dispersion of a halogenated heterocyclic N-halamine in an inert liquid carrier to the surface of the article and allowing the inert liquid carrier to penetrate into the article, wherein the inert liquid carrier does not react with halogen atoms in the halogenated heterocyclic N-halamine, and wherein the halogenated heterocyclic N-halamine becomes deposited on the surface of the article after the inert liquid carrier penetrates into the article. This method can be used to provide a high level of odor resistance to a wide variety of substrates. It is of particular value for use in manufacturing garbage bags having a high level of odor resistance. In some embodiments of this invention odor control is achieved by antimicrobial activity and/or enzyme inhibition.

In another embodiment of this invention toxins and other undesirable materials can be removed from water or air by means of chemical degradation/oxidation or high affinity adsorption. This is typically accomplished by depositing the desired active material onto a suitable filter through which the water or air flow being treated passes. The toxin is normally removed from the water or air stream by adsorption, chemical degradation, or oxidation. In any case, the methodology of this invention is used for the detoxification of water or air to make it more suitable for coming into contact with humans or animals.

One embodiment of this invention more specifically relates to method of manufacturing an odor resistant plastic film which comprises applying a dispersion of a halogenated heterocyclic N-halamine in an inert liquid carrier to the surface of the thermoplastic film and allowing the inert liquid carrier to penetrate into the plastic film, wherein the inert liquid carrier does not react with halogen atoms in the halogenated heterocyclic N-halamine. In one specific embodiment of this invention the plastic film is in the form of a garbage bag, trash bag, or bin bag. Trash bags are normally made from polyethylene because it is tough, puncture resistant, light, and flexible. Due to its relatively low cost low density polyethylene is typically used. However, in applications were higher strength bags are needed high density or linear low density polyethylene can also be utilized.

In manufacturing garbage bags molten polyethylene is extruded, typically at a temperature which is within the range of 365° F. to 465° F., through a die into a ring. The ring is then blown into a bubble and cooled to below its melting point into a long tube. Then, rollers are used to collapse the bubble into a flat tube. The flat tube is then cut to the desired length and heat-sealed on one end with the other end remaining open. Next, the trash bags are then folded, stacked, and inserted into their packaging for use by a consumer. Such bags are make to be odor resistant in accordance with this invention by applying, typically spraying, a dispersion of a halogenated heterocyclic N-halamine in an inert liquid carrier onto the surface of the inside or outside of the bag and then allowing the inert liquid carrier to penetrate into the walls of the bag leaving particles of the halogenated heterocyclic N-halamine walls of the bag. The walls of such trash bags are normally 0.0002 inch to 0.005 inch thick.

This invention accordingly relates to a garbage bag having walls which are comprised of polyethylene, wherein said walls of the garbage bag are coated with particles of a halogenated heterocyclic N-halamine having a particle size which is within the range of about 0.01 μm to 20 μm, and wherein the particles of the halogenated heterocyclic N-halamine are present only of the surface of the walls of the garbage bag.

In another embodiment of this invention relates to a method for manufacturing a medium for purifying fluids which comprises applying a dispersion of a micronized metal oxide in an inert liquid carrier to the surface of a substrate having a high surface area and allowing the inert liquid carrier to penetrate into the substrate leaving the micronized metal oxide stranded on the surface of the substrate. The micronized metal oxide utilized in this embodiment of the invention will typically have a high affinity for sequestering contaminants, such as toxic metals.

This invention also provides a method for manufacturing a medium for purifying fluids containing toxic compounds which comprises applying a dispersion of a halogenated heterocyclic N-halamine in an inert liquid carrier to the surface of a substrate having a high surface area and allowing the inert liquid carrier to penetrate into the substrate, wherein the inert liquid carrier does not react with halogen atoms in the halogenated heterocyclic N-halamine, wherein the halogenated heterocyclic N-halamine is capable of destroying the toxic compound by oxidative action, and wherein the halogenated heterocyclic N-halamine becomes deposited on the surface of the substrate after the inert liquid carrier penetrates into the substrate. This medium can be beneficially employed in removing toxic gases from the air and other gases. For instance, it can be used in purifying air that has been contaminated with nerve gas, mustard gas and other gases used in chemical warfare.

The subject invention also provides a deodorizing solution which is comprised of an organic liquid and a halogenated heterocyclic N-halamine, wherein the organic liquid does not react with halogen atoms in the halogenated heterocyclic N-halamine, and wherein the halogenated heterocyclic N-halamine is soluble with the organic liquid. This deodorizing solution is of great value in deodorizing toilets and urinals.

Air filters can be made in accordance with this invention by treating conventional air filtration media with a dispersion of a halogenated heterocyclic N-halamine in an inert liquid carrier. Such air filters are highly efficient with respect to removing a wide variety of organic contaminants from air streams. In a preferred embodiment of this invention conventional HEPA (high-efficiency particulate arrestance) filters can be treated with the liquid dispersion of this invention to produce filters that are highly efficient at removing both particulate matter and organic compounds from air streams. It should be noted that conventional HEPA filters must be capable of removing at least 99.97% of particles having a size of 0.3 μm. In any case, such filters can be beneficially used in commercial, industrial, and residential settings, such as hospitals, clinics, offices, stores, factories, warehouses, chemical plants, apartment buildings, and homes. The air filters of this invention can be incorporated into the central heating/cooling system of buildings, exhaust systems, intake systems, or as stand-alone room filters. They can also be used in automobile and aircraft cabin filters.

A number of states now allow for the use of marijuana for medical and in some cases recreational purposes. This has created a demand for air filters that can effectively remove odors associated with the production and burning of marijuana from greenhouses where it is grown, from the exhaust gases emitted from such greenhouses, and from buildings where marijuana is ultimately used. Air filtration media which has been treated with a dispersion of a halogenated heterocyclic N-halamine in an inert liquid carrier is highly useful for these purposes.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not limit the scope of the invention described herein.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as delineated in the claims hereof.

Halogenated heterocyclic N-halamines are utilized in several embodiments of this invention. It is typically preferred for the halogenated heterocyclic N-halamine to be a partially halogenated hydantoin. These partially halogenated hydantoins are generally of the structural formula:

where $X_1$ and $X_2$ independently represent hydrogen atoms or halogen atoms and $R_1$ and $R_2$ independently represent linear or branched alkyl groups containing from 1 to about 10 carbon atoms. It is normally preferred for $R_1$ and $R_2$ represent an alkyl group containing from 1 to 4 carbon atoms. It is also normally preferred for the halogen atoms in the partially halogenated hydantoins to be chlorine atoms or bromine atoms. Some representative examples of partially halogenated hydantoins that can be employed in the practice of this invention include $Cl_{0.5\text{-}5,5}$-dimethyl hydantoin, $Cl_{0.9\text{-}5,5}$-dimethyl hydantoin, $Cl_{1.1\text{-}5,5}$-dimethyl hydantoin, $Cl_{1.05\text{-}1.4\text{-}5,5}$-dimethyl hydantoin, monochloro-5,5-dimethyl hydantoin (MCDMH), $Br_{0.9\text{-}5,5}$-dimethyl hydantoin, monobromo-5,5-dimethyl hydantoin (MBDMH), $Cl_{0.5\text{-}5}$-methyl-5-ethyl hydantoin, $Cl_{0.9\text{-}5}$-methyl-5-eth-yl hydantoin, $Cl_{1.1\text{-}5}$-methyl-5-ethyl hydantoin, $Cl_{1.05\text{-}1.4\text{-}5}$-methyl-5-ethyl hydantoin, monochloro-5-methyl-5-ethyl hydantoin, $Br_{0.9\text{-}5}$-methyl-5-ethyl hydantoin, and monobromo-5-methyl-5-ethyl hydantoin. Some preferred partially halogenated hydantoins include $Cl_{0.9\text{-}5,5}$-dimethyl hydantoin, $Cl_{0.9\text{-}5}$-methyl-5-ethyl hydantoin, $Cl_{1.1\text{-}5,5}$-dimethyl hydantoin, and $Cl_{1.1\text{-}5}$-methyl-5-ethyl hydantoin. Monochloro-5,5-dimethyl hydantoin is the highly preferred partially halogenated hydantoin for utilization in the practice of this invention.

Some representative examples of additional halogenated heterocyclic N-halamines that can be used in the practice of this invention include N-chloro-N-sodiomethylbenzenesulfonamidate trihydrate, N,N-dichloro-4-methylbenzenesulfonamide, N-bromo-N-sodio-4-nitrobenzenesulfonamidate, N,N-dichlorobenzenesulfonamide, N-chloro-N-sodiobenzenesulfonamidate, mono-chlorosulfamate, dichlorosulfamate, N-chloroimidodisulfonates, sodium N-chloro-N-arylsulfamates, 2,4,6,8-tetrachloro-2,4,6,8-tetrazobicyclooctane-3,7-dione, sodium trichloroimidometaphosphamate, N-halosulfinylamines, N-halo-N-sodioamidates, chloroisocyanurates, N-halocarbamidates, N-halosulfonamidates, N-chloro-imidodisulfonate, N,N-dichloromethylamine, 2-chloro-1,3,5-triazine-2,4,6-triamine, 2,4-dichloro-1,3,5-triazine-2,4,6-triamine, 2,4,6-trichloro-1,3,5-triazine-2,4,6-triamine, 1-chloro-5,5-dimethylhydantoin, 1-bromo-5,5-dimethylhydantoin, 1,3-dibromo-5,5-dimethylhydantoin 1-chloro-3-bromo-5,5-dimethylhydantoin, 1,3-dichloro-5,5-dimethylhydantoin, 1-chloro-4,4,5,5-tetramethylimidazolidin-2-one, 1,3-dichloro-4,4,5,5-tetramethylimidazolidin-2-one, 1-chloro-2,2,5,5-tetramethylimidazolidin-4-one, 1,3-dichloro-2,2,5,5-tetramethylimidazolidin-4-one, 1,3-dichloro-s-triazine-2,4,6-trione, trichloroisocyanuric acid, potassium dichloroisocyanurate, sodium dichloroisocyanurate, potassium dibromoisocyanurate, sodium dibromoisocyanurate, mono to hexachloromelamine, mono to hexabromomelamine, 3-chloro-4,4-dimethyl-2-oxazolidinone, N-chlorosuccinimide, 1-chloropyrrolidine-2,5-dione, 1,3-dichlorotetrahydroquinazoline-2,4-dione, 1,4-dichloro-2,2,5,5-tetrasubstituted-piperazine-3,6-diones, N-chloro-2,2,6,6-tetramethylpiperidine, N-chloro-4-amino-2,2,6,6-tetramethylpiperidine, polymer-bound N-chloro-N-sodiobenzenesulfonamidates, chlorinated polyacrylamide, brominated polyacrylamide, chlorinated poly(methacrylamide), brominated poly(methacrylamide), poly(N-chloro-2,2,6,6-tetramethyl-4-piperidinyl acrylate), poly(N-chloro-hydantoin-methyl-p-styrene) emulsion, 1-chloro-3-bromoalkyltrimethylammonium-4,4,5,5-tetramethyl imidazolidin-2-one, 1-bromo-3-bromoalkyltrimethylammonium-4,4,5,5-tetramethyl imidazolidin-2-one, 1-chloro-3-bromoalkyltrimethylammonium-2,2,5,5-tetramethyl imidazolidin-4-one, 1-bromo-3-bromoalkyltrimethylammonium-2,2,5,5-tetramethyl imidazolidin-4-one, 2-chloro-4-bromoalkyltrimethylammonium-1,3,5-triazine-2,4,6-triamine, 2-bromo-4-bromoalkyltrimethylammonium-1,3,5-triazine-2,4,6-triamine, 1-chloro-3-bromoalkyltrimethylammonium-5,5-dimethylhydantoin, and 1-bromo-3-bromoalkyltrimethylammonium-5,5-dimethylhydantoin.

Some embodiments of this invention utilize an inert liquid carried which does not react with halogen atoms in halogenated heterocyclic N-halamines. The inert liquid carrier can be a vegetable based ester of the structural formula: $CH_3(CH_2)_n COOCH_x(CH_3)_y$, wherein n represents an integer which is within the range of 6 to 22, wherein x represents an integer which is within the range of 0 to 3, wherein y represents an integer which is within the range of 0 to 3, and wherein the sum of x and y is 3. The inert liquid carrier will normally be of the structural formula: $CH_3(CH_2)_n COOCH(CH_3)_2$, wherein n represents an integer which is within the range of 6 to 22. The integer n will typically be within the range of 8 to 18 and is preferably within the range of 10 to 14. Isopropyl myristate which is of the structural formula: $CH_3(CH_2)_{12}COOCH(CH_3)_2$ is an example of a highly preferred inert liquid carrier.

In one embodiment of this invention an odor resistant article is made by applying a dispersion of a halogenated heterocyclic N-halamine in an inert liquid carrier to the surface of the article and allowing the inert liquid carrier to penetrate into the article, wherein the inert liquid carrier does not react with halogen atoms in the halogenated heterocyclic N-halamine, and wherein the halogenated heterocyclic N-halamine becomes deposited on the surface of the article after the inert liquid carrier penetrates into the article. The articles which can be made odor resistant in accordance with this invention are typically comprised of a solid material selected from the group consisting of plastics, natural rubber, synthetic rubber, wood, porous inorganic materials, and fibers. In many cases the article will be comprised of a solid porous substrate. Some representative examples of porous inorganic material that the article can be comprised of include aluminosilicate, kaolinite, montmorillonite-smectite, illite, and chlorite. Some representative examples of fibers include cotton fibers, wool fibers, nylon fibers, polyester fibers, and aramid fibers. The article can also be comprised of a wide variety of solid materials, such as plastics, including polyolefins, polyamides, polyesters, polyurethanes, polycarbonates, and the like. For instance, the plastic can be low density polyethylene, linear low density polyethylene, high density polyethylene, or polypropylene. In one mode of operation the halogenated heterocyclic N-halamine provides odor resistance by deactivating enzymes.

The inert liquid carrier can be applied to the surface of the article being treated by using a wide variety of techniques. The optimum technique is dependent upon the nature of the article and its geometric structure. In any case, the inert liquid carrier can typically be sprayed onto the surface of the article. In some cases, it is convenient to apply the inert liquid carrier with a brush or to dip the article into a bath of the inert liquid carrier.

The halogenated heterocyclic N-halamine will normally be dispersed in the inert liquid carrier in the form of particles which are in the particle size range of about 0.01 µm to 20 µm. The particles of the halogenated heterocyclic N-halamine will typically have a particle size which is within the range of about 0.05 µm to 15 µm, and will more typically be of particles size which is within the range of about 0.1 µm to 12 µm. The particles of the halogenated heterocyclic N-halamine will preferably have a particle size which is within the range of about 0.1 µm to 10 µm, and will more preferably be of particles size which is within the range of about 0.5 µm to 8 µm. In many cases the halogenated heterocyclic N-halamine will be of a particle size which is within the range of about 1 µm to 6 µm, and will frequently be of particles size which is within the range of about 3 µm to 5 µm.

The halogenated heterocyclic N-halamine will typically be dispersed in the inert liquid carrier at a level which is within the range of about 0.01 weight percent to about 50 weight percent. The halogenated heterocyclic N-halamine will more typically be dispersed in the inert liquid carrier at a level which is within the range of about 0.05 weight percent to about 25 weight percent. The halogenated heterocyclic N-halamine will normally be dispersed in the inert liquid carrier at a level which is within the range of about 0.1 weight percent to about 10 weight percent and will preferably be dispersed in the inert liquid carrier at a level which is within the range of about 0.4 weight percent to about 5 weight percent. In many cases the halogenated heterocyclic N-halamine will be dispersed in the inert liquid carrier at a level which is within the range of about 0.6 weight percent to about 2 weight percent. The halogenated heterocyclic N-halamine will frequently be dispersed in the inert liquid carrier at a level which is within the range of about 0.8 weight percent to about 1.5 weight percent. It is preferred for the halogenated heterocyclic N-halamine is insoluble in the inert liquid carrier.

The method of this invention is highly useful for treating thermoplastic film to make it odor resistant. For instance, treating garbage bags in accordance with the method of this invention to make them odor resistant is of particular commercial importance. In such a method a dispersion of a halogenated heterocyclic N-halamine in an inert liquid carrier is applied to the plastic film and the inert liquid carrier is allowed to penetrate into the plastic film leaving a coating of halogenated heterocyclic N-halamine particles on the surface of the film. The dispersion of the halogenated heterocyclic N-halamine in the inert liquid carrier is typically sprayed onto the surface of the film. As has previously been explained, it is important for the inert liquid carrier not to react with halogen atoms in the halogenated heterocyclic N-halamine. In any case, it is important for particles of the halogenated heterocyclic N-halamine to become deposited on the surface of the plastic film after the inert liquid carrier penetrates into the film. In many cases the plastic film will be a polyolefin film, such as a polyethylene film. Low density polyethylene is useful in a wide variety of applications. As has been previously explained, in some cases the halogenated heterocyclic N-halamine provides odor resistance by deactivating enzymes.

In another embodiment of this invention other solid stable particulate oxidants, such as potassium monopersulfate and permanganates can be substituted for N-halamines in certain applications and by the judicious selection of liquid vehicles that are compatible with the deposition of the unreacted particulates on substrate surfaces. For example, a method for manufacturing a medium for purifying fluids can be made using such a rationale. This method involves applying a dispersion of a micronized metal oxide in an inert liquid carrier to the surface of a substrate having a high surface area and allowing the inert liquid carrier to penetrate into the substrate leaving the micronized metal oxide stranded on the surface of the substrate. In such applications, the micronized metal oxide will have a high affinity for sequestering contaminants, such as toxic metals.

Another embodiment of this invention relates to a deodorizing solution which is comprised of an organic liquid and a halogenated heterocyclic N-halamine, wherein the organic liquid does not react with halogen atoms in the halogenated heterocyclic N-halamine, and wherein the halogenated heterocyclic N-halamine is soluble with the organic liquid. The halogenated heterocyclic N-halamine is normally a partially halogenated hydantoin. In such deodorizing solutions the halogenated heterocyclic N-halamine will normally be present in the inert liquid carrier (the organic liquid) at a level which is within the range of 0.1 weight percent to about 5 weight percent, based upon the total weight of the deodorizing solution. The halogenated heterocyclic N-halamine will typically be present in the inert liquid carrier at a level which is within the range of 0.1 weight percent to about 4 weight percent, based upon the total weight of the deodorizing solution and will more typically be present at a level which is within the range of 0.2 weight percent to about 3 weight percent, based upon the total weight of the deodorizing solution. The halogenated heterocyclic N-halamine will preferably be present in the inert liquid carrier at a level which is within the range of 0.5 weight percent to about 2.5 weight percent, based upon the total weight of the deodorizing solution and will more preferably be present at a level which is within the range of 1 weight percent to about 2 weight percent, based upon the total weight of the deodorizing solution. A wide variety of substrates can be deodorized by simply applying this deodorizing solution to the surface thereof.

In accordance with this invention, an aqueous medium can be deodorized by dispensing an amount of the deodorizing solution which is sufficient to form an organic layer which extends substantially over the surface of the aqueous medium being deodorized. For example, a toilet bowl or urinal can be deodorized by dispensing the deodorizing solution into the water in the toilet bowl or the urinal. The deodorizing solution is typically dispensed into the toilet bowl or the urinal upon being flushing. For instance, the deodorizing solution can be dispensed into the toilet bowl with the water that refills the toilet bowl after the toilet is flushed. In deodorizing a toilet bowl it is preferable for the deodorizing solution to be dispensed into the toilet bowl at a level which is sufficient to coat the sides of the toilet bowl above the water line and to provide an organic layer which extends substantially over the surface of the water in the toilet bowl.

If the solid substrate is buoyant, as may be the case for certain forms of aluminosilicate (such as vermiculite), or organic particulates with a low demand for oxidants (such as sawdust derived from hardwoods, or certain subsets of nut shells) or certain synthetic porous polymers (such as porous polypropylene), the microparticles applied to the surface using the methods described above for zeolite can result in a coating, able to float on the surface of aqueous media, that confers on the modified solid substrate a powerful capacity to contain and neutralize malodorants emanating from toilet waste or agricultural manure slurries. Such preparations can be of value in deodorizing latrines, portable toilets, toilets in marine vessels, aircraft toilets, recreational vehicles (RVs), livestock manure lagoons, and the like. In many applications of this type the buoyant material is particularly effective because it is dispersed on the surface of the liquid being deodorized.

Still another embodiment of this invention relates to a method for manufacturing a medium for purifying fluids containing toxic compounds which comprises applying a dispersion of a halogenated heterocyclic N-halamine in an inert liquid carrier to the surface of a substrate having a high surface area, such as a conventional air or liquid filter, and allowing the inert liquid carrier to penetrate into the substrate. It is important for the inert liquid carrier not to react with halogen atoms in the halogenated heterocyclic N-halamine. It is also important for the halogenated heterocyclic N-halamine to be capable of destroying the toxic compound, such as toxic gases including nerve gas or mustard gas, by oxidative action, and for the halogenated heterocyclic N-halamine to become deposited on the surface of the substrate after the inert liquid carrier penetrates into the substrate. The techniques of this invention can be used to deodorize hard surfaces, such countertops, which are comprised of a metal, a ceramic, tile, glass, masonry, wood, porcelain, stone, polymeric materials, and the like.

Air and water filters can be manufactured in accordance with this invention to deodorize air or water by treating the filtration medium with a dispersion of a halogenated heterocyclic N-halamine in an inert liquid carrier. For instance, the air filtration medium can be a HEPA filter. The filtration material can be comprised of a multitude of non-woven polyester fibers which are bound together with an ethylene-vinyl chloride copolymer binder into the form of a sheet. The polyester used in making the non-abrasive fabric is typically polyethylene terephthalate or polyethylene naphthalate having an intrinsic viscosity which is within the range of 0.45 dl/g to about 0.85 dl/g. The polyester will more typically have an intrinsic viscosity which is within the range of 0.50 dl/g to about 0.75 dl/g and will normally have an intrinsic viscosity which is within the range of 0.50 dl/g to about 0.70 dl/g. In most cases the polyester will have an intrinsic viscosity which is within the range of 0.55 dl/g to about 0.65 dl/g. It is normally preferred to utilize a polyester having an intrinsic viscosity which is within the range of 0.60 dl/g to about 0.64 dl/g. Polyethylene terephthalate (PET) resins that are useful in the practice of this invention are commercially available from Gruppo Mossi & Ghisolfi and Eastman Chemical). For instance, Cleartuf® P60 PET resin which has an intrinsic viscosity of 0.58 dl/gram, an acetaldehyde content of <80 mg/kg, and a melting point of 250° C. can be used in manufacturing the non-woven fabric. Cleartuf® P76 PET resin which has an intrinsic viscosity of 0.74 dl/gram, an acetaldehyde content of 1.0 ppm, and a melting point of 250° C. can optionally be used in manufacturing the non-woven fabric.

The fabric used for filtration is typically comprised of a multitude of non-woven polyester fibers which are bound together in the form of a sheet with an ethylene-vinyl chloride copolymer binder. The polyester fibers in the non-woven fabric typically have a diameter which is within the range of about 10 micrometers to about 50 micrometers and more have a diameter which is within the range of about 15 micrometers to about 40 micrometers. In most cases the polyester fibers have a diameter which is within the range of about 20 micrometers to about 30 micrometers. It is normally preferred for the polyester fibers have a diameter which is within the range of about 22 micrometers to about 27 micrometers.

The non-woven fabric of the filtration material will typically have a density which is within the range of about 0.01 grams/cc to about 0.40 grams/cc and will more typically have a density which is within the range of about 0.02 grams/cc to about 0.30 grams/cc. In most cases the filtration medium will have a density which is within the range of about 0.03 grams/cc to about 0.20 grams/cc. It is normally preferred for the filtration medium (fabric) to have a density which is within the range of about 0.04 grams/cc to about 0.15 grams/cc. It is generally more preferred for the fabric to have a density that is within the range of about 0.05 grams/cc to about 0.10 grams/cc. It is normally most preferred for the fabric to have a density that is within the range of about 0.06 grams/cc to about 0.08 grams/cc.

The ethylene-vinyl chloride polymer (EVC) binder utilized in manufacturing the filtration medium fabric can optionally be crosslinked with an external crosslinker, such as melamine or a urea formaldehyde resin to achieve improved wet tensile properties. The use of ethylene-vinyl chloride polymer emulsions as binders for nonwoven fabrics is described in U.S. Pat. No. 7,247,568. The teachings of U.S. Pat. No. 7,247,586 are incorporated herein by reference for the purpose of teachings the types of ethylene-vinyl chloride polymer emulsions that can be used in manufacturing filtration material and a for the purpose of teaching methods for manufacturing fabric filtration materials with such EVC binders.

This invention is illustrated by the following examples which are merely for the purpose of illustration and are not to be regarded as limiting the scope of the invention or the manner in which it can be practiced. Unless specifically indicated otherwise, parts and percentages are given by weight.

Example 1

Figure 1:
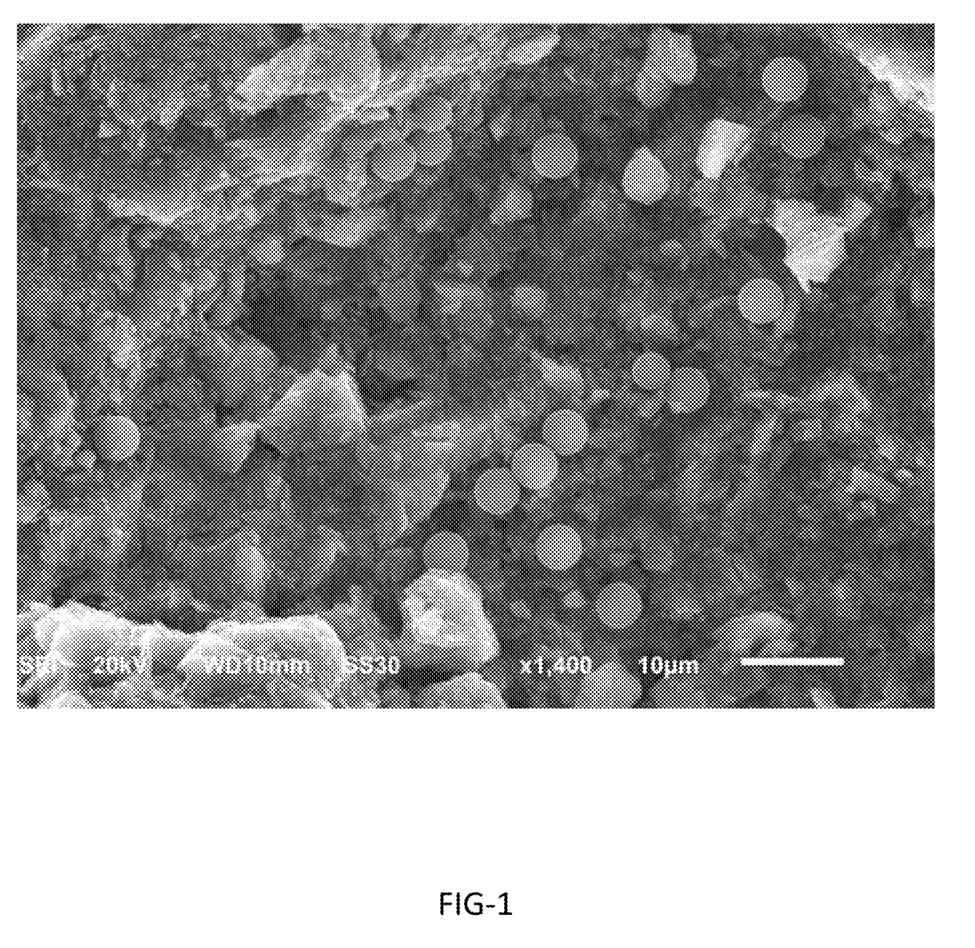
FIG. 1 is a SEM image of a zeolite substrate which has been coated with 5 micron particles in accordance with this invention as described in Example 1.
Figure 2:
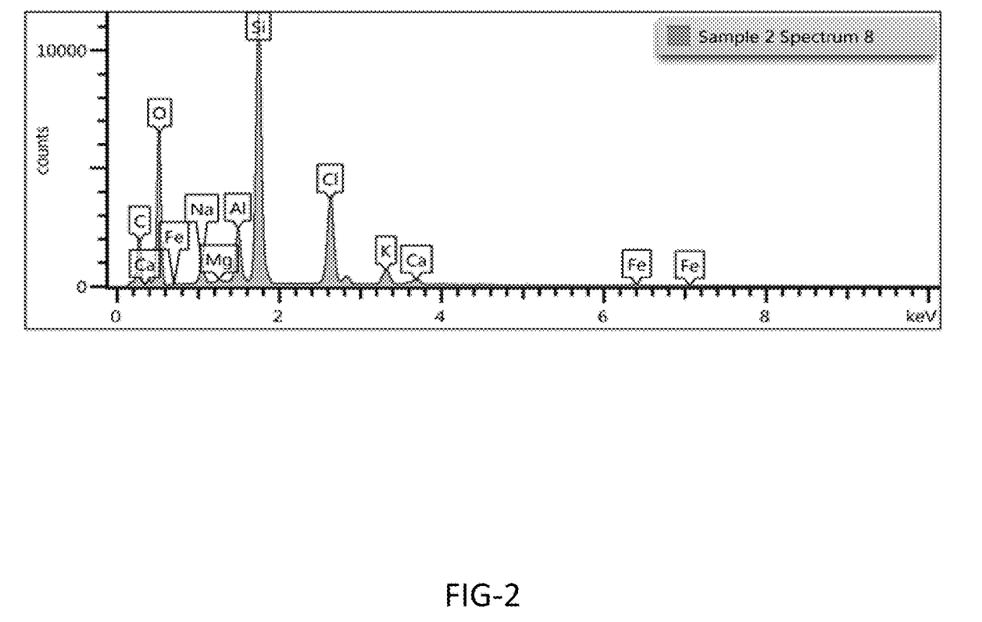
FIG. 2 is an EDS line scan of a zeolite substrate which has been coated with 5 micron particles in accordance with this invention as described in Example 1.

The objective of this experiment was to demonstrate that when natural zeolite granules are exposed to a dispersion of particles of approximately 5 microns the absorption of the liquid vehicle into the porous zeolite leaves the micro particles exposed on the surface of the aluminosilicate granules. Latex spheres having an average diameter of 5 microns were purchased from Sigma Aldrich Inc, St. Louis, Mo., and suspended as a dispersion in water, since they are not soluble in this medium. Then, clinoptilolite aluminosilicate zeolite granules (14×40 mesh) were mixed with the dispersion until the fluid had soaked into the substrate. Samples were then vacuum dried and coated for scanning electron microscopy (SEM). Images of the surface of the zeolite showed a coating of 5 micron particles present in the crevices and voids of the coarsely irregular outer surface. This SEM image is shown in FIG. 1. Latex spheres were used because their uniform shape made them readily identifiable against the irregular background micro-topography of the zeolite. Micronized particles of the N halamine were irregular in shape and not clearly distinguishable from the background by SEM. However, when the surface was scanned using Energy Dispersive X-Ray Spectroscopy (EDS) a clear signal for surface chlorine was detected at 2.3 keV against the aluminosilicate background in SEM. The EDS line scan of the surface of the zeolite granules exposed to a dispersion of N-halamine micronized particles (5 microns average diameter) suspended in an inert organic vehicle after absorption of the vehicle into the porous matrix to the zeolite is shown in FIG. 2. N-halamine particles on the surface contain chlorine, clearly identifiable against the background of aluminosilicate elemental constituents detected by this technique. This experiment illustrates the principle of coating micronized particles onto porous substrates using a dispersion of the active particles.

Example 2

This experiment was performed to illustrate the method of manufacturing an odor resistant animal litter. In the procedure used twenty grams (20 g.) of micronized 1-chloro-5, 5-dimethylhydantoin and 5 grams micronized 1-chloro-2,2, 5,5-tetramethylimidazolidin-4-one with size around 5 um were dispersed into 40 grams of isopropyl myristate, and agitated for 30 minutes. The resulting mixture was a white and stable dispersion. The dispersion was sprayed onto 2 kg of Montmillorite zeolite granules with a spray painting gun. The treated zeolites did not show obvious visible changes. The coating can be expected to significantly reduce the fine dust particles in litter. The treated zeolite was found to react with a 1% solution of potassium iodide to produce a deep brown color, indicative of the presence of oxidant power on the surface of the N-halamine coated granules. This reactivity on contact with potassium iodide persisted unchanged for many months of storage at room temperature.

Example 3

The purpose of this experiment was to illustrate the means of characterizing the coated granular medium by titration of the active chlorine contents. In the procedure used coated zeolite Cl contents were determined by iodometric titration.

Approximately one half gram of coated zeolite granules was ground into fine powder, and treated with 1 g of potassium iodide (KI) in 100 mL of deionized water (the solution contained 0.05% (v/v) of TX-100). The mixture was stirred constantly at room temperature for 1 hour. The molecular iodine formed ($I_2$) was titrated with standardized aqueous sodium thiosulfate solution. Uncoated zeolite granules were tested under the same conditions to serve as controls. The available active chlorine content on the zeolites was calculated according to equation (1):

$$Cl\ \% = \frac{35.5}{2} \times \frac{(V_S - V_0) \times C_{Na_2S_2O_3}}{W_S} \times 100 \quad (1)$$

where $V_S$, $V_0$, $C_{Na2S2O3}$ and $W_S$ were the volumes (mL) of sodium thiosulfate solutions consumed in the titration of the coated and uncoated samples, the concentration (moles/L) of the standardized sodium thiosulfate solution, and the weight of the chlorinated sample (mgram), respectively. By adjusting the N-halamine concentration in the treatment process, it was determined that a series of coated zeolites could be prepared with active chlorine contents of 654, 1143, and 2057 ppm, respectively.

Example 4

The purpose of this experiment was to illustrate the method of manufacturing an odor resistant plastic film coating. Twenty grams (20 g) of micronized 1-chloro-5,5-dimethylhydantoin and 2 grams of micronized 1-chloro-2,2,5,5-tetramethylimidazolidin-4-one (average particle size approximately 5 um) were dispersed into 20 grams of isopropyl myristate, and agitated for 30 minutes. The resulting mixture was a white and stable dispersion. For each LDPE plastic bag serving as substrate for the coating procedure, 0.5 gram of the resulting dispersion was applied onto the inner surface with a fabric wiper. The treated plastic bag did not show obvious visible changes, other than a very slight oily sheen that disappears after several days of storage. Chlorine titration of the active coated plastic showed a content of 150 mgram per square meter.

Example 5

The purpose of this experiment was to illustrate the method of manufacturing an odor resistant article. Ten grams (10 g) of micronized 1,3-dichloro-5,5-dimethylhydantoin and 2 grams micronize 1-chloro-2,2,5,5-tetramethylimidazolidin-4-one with an average size of about 5 um were dispersed into 30 grams of vegetable-based ester, agitated for 30 min; the resulting mixture was a white and stable dispersion. The resulting dispersion was sprayed onto 2 kg hydrated calcium silicate granules with a sprayer bottle. The treated calcium silicate granules did not show obvious changes. The coating can be expected to significantly reduce the fine dust particles from the litter during normal use. Chlorine titration indicated the presence of 576 ppm active chlorine.

Example 6

The purpose of this experiment was to demonstrate the microparticles of N-halamine coated onto zeolite granules could have odor control effects on offensive malodorants when in direct contact with these substances. This was accomplished by exposing 3-mercapto-3 methyl 1 butanol (3M3 MB) to uncoated zeolite granules as a negative control or to zeolite exposed to a dispersion of the micronized N halamine. Aliquots (1.5 g) of each sample were added to 5 mL of 1 mM 3M3 MB in 50 mM MES buffer containing 150 mM KCl at pH 6.2. The suspensions were mixed well before serial sampling of the supernatants obtained at each time point by centrifuging the mixtures at 8000 rpm for 20 seconds. Supernatants (50 µL) were added to cuvettes containing 50 µL of 20 mM DTNB solution and 900 µL of 50 mM MES buffer at pH 6.8. The absorbance of TNB⁻ was measured at 412 nm. A calibration curve in 50 mM MES buffer at pH 6.8 had been prepared giving an extinction coefficient of 13986 $M^{-1}\ cm^{-1}$.

The results showed that whereas in the negative control there was only a 0.5% reduction in the amount of thiol detected spectrophotometrically after exposure, the reduction after contact with the N-halamine coated granules was 99.5%. These data indicate that the micronized particle coated medium may exert powerful malodor control by direct chemical degradative effects on targets such as thiols.

Example 7

In this experiment the effect of contact of a malodorant (3M3 MB) with micronized coated zeolite granules was measured in the headspace above the reaction mixtures using GC MS procedures. A solution (2 mL) containing 100 ppm 3M3 MB and 200 ppm β-mercaptoethanol in 50 mM phosphate buffer pH 7.0 was added to 500 mg of each litter in a 10 mL Supelco glass headspace vial. Headspace analysis was done using a Supelco SPME PDMS/Carboxen 75 µm fiber and an adsorption time of 10 minutes. This fiber was chosen based on the molecular weight of the compounds used. Before use and in between each type of litter, a fiber blank was performed in order to clear the fiber of potential residues from earlier runs. An Agilent 6850 series GC with a 0.75 mm×6.35×78.5 inlet liner was used. The oven settings were programmed to 40° C. for 5 minutes, then ramping up to 125° C. at 8.5° C./minute for a total of 15 minutes. The column had a flow rate of 1.2 mL/meter and the detector temperature was set at 300° C. The inlet temperature was set to 250° C. with the pressure at 9.14 psi. The mass spectrophotometer used was an Agilent 5973 Network Mass Selective Detector. The headspace was analyzed four times for each of the negative control and the coated zeolite samples. The ratio of the 3M3 MB to β-mercaptoethanol peak areas, and the ratios of the oxidized 3M3 MB to β-mercaptoethanol peak areas were averaged, and a standard deviation calculated for each test condition.

The ration of the thiol to mercaptoethanol standard for the negative control was approximately 4.5:1. There was no thiol detectable in the headspace above the mixture of 3M3 MB with the N-halamine-coated zeolite granules. These results indicate that the direct degradative effect of the coated zeolite can lead to rapid and complete elimination of commonplace malodorants such as sulfanyl butanol. Similar findings were observed for a related sulfanyl hexanol compound. Since sulfur containing inorganic (e.g., H2S) and organic compounds can be toxic and/or irritants this result may be taken also to mean that the medium may be useful in detoxification of contaminated fluids or flows of air.

Example 8

In this experiment the effectiveness of micronized N-halamine coated zeolite granules was tested in a system that was evaluated by a panel of human subjects exposed to the headspace above the reaction mixtures. Sensory evaluation of the efficacy versus 3M3 MB was determined by comparing uncoated zeolite as a negative control with the coated material. 125 mL of the two test samples plus the control zeolites in 1.25 L glass vessels were assessed for their capacity to affect the headspace scores assigned by a ten-member panel after the addition of 1 mL of 1% w/w of 3M3 MB. Vessels were securely covered, and allowed to equilibrate for four hours prior to scoring. Beakers were coded with random numbers, and presented to judges in irregular order. Judges participated in a training session to clearly understand the sensory attributes to be scored, and to practice the evaluation protocol. Each judge scored the test headspaces as either acceptable (0) or offensive (10), or at some level in between.

All judges found the thiol odor in the negative control zeolite to be offensive. Nine scored the sample incubated with the N-halamine coated positive control as acceptable. No intermediate scores were assigned by any of the judges. These results demonstrate the utility of the coated medium in affecting the mitigation of malodor perceived by human subjects exposed to a sulfurous organic compound.

Example 9

The purpose of this experiment was to demonstrate the odor control effectiveness of micronized N-halamine particle-coated zeolite granules when used as a top dressing or sprinkle on the surface of conventional cat litter challenged with a volatile urine malodorant. In the procedure used two grams (2 g) of commercial cat litter granules (Catsan by Mars Inc, or Double Duty by Church and Dwight Inc.) or 2 gm of uncoated zeolite granules as control were placed in 10 mL glass vials. To these samples were added 1 ml aliquots of an aqueous solution containing 100 ppm 3-mercapto-3-methylbutan-1-ol as a urine-derived malodorant. Test flasks were treated with either a top dressing of 100 mg of Arm and Hammer Double Duty odor control sprinkles or 100 mgs of micronized N-halamine-coated zeolite particles from Oxi-Science LLC, Redmond Wash.

Headspace analysis was done using GC/MS by absorbing a gas sample onto a Supelco SPME PDMS/Carboxen 75 um fiber, placed in the headspace for 10 minutes. The fibers were then placed in an Agilent 6850 series GC with a 0.75 mm×6.35×78.5 inlet liner. The oven settings were programmed to 40° C. for 5 minutes, then ramping up to 125° C. at 8.5° C./minute for a total of 15 minutes. The column had a flow rate of 1.2 mL/meter and the detector temperature was set at 300° C. The inlet temperature was set to 250° C. with the pressure at 9.14 psi. The mass spectrophotometer used was an Agilent 5973 Network Mass Selective Detector. Collected molecular weight 45-190 g/mol. Each experimental and control vial sample was set up in triplicate.

No detectable thiol was present in the headspace of the vials that were sprinkled with the N-halamine coated zeolite. The vials containing cat litter had 10.5, 11.2 and 9.4 ngm of thiol for the Arm and Hammer Double Duty, Catsan and Zeolite (control), respectively. Sprinkling with Arm and Hammer Odor Control litter top dressing had no effect on the malodorant levels.

This result shows that N-halamine coated zeolite is effective at controlling cat urine odors caused by volatile thiols, even when used as a top dressing on conventional litter granules that are themselves ineffective in affecting the malodorant.

Example 10

The purpose of this experiment was to demonstrate the antibacterial activity of zeolite granules coated with micronized N halamine particles. This was determined in a contact test using a urease positive strain of *Proteus vulgaris* bacteria. Bacterial suspensions in broth culture were washed in sterile phosphate buffer (PBS) solution, sedimented by centrifugation, and resuspended in PBS at 108 cfu/ml for the challenge. One milliliter was added to 5 g of the test sample of N halamine coated zeolite (in triplicate), and to triplicates of negative (uncoated) zeolite controls. After measured contact times, 20 mL 0.03 weight percent sodium thiosulfate aqueous solution was added to each sample so as to quench the active chlorine in the N halamine particles in the positive controls. The mixtures were vortexed for 1 minute, and sonicated for 5 minutes, before plating 10 µl aliquots from serial dilutions onto agar plates for colony counts after incubation at 37° C. for 24 hours.

Exposure to the N halamine-coated zeolite produced a log reduction value (LRV) of 6 (i.e., 99.9999%) at all time points tested, compared to control. This result shows the utility of coated zeolite in inhibiting the growth of an odor-causing microbe (*P. vulgaris*), as a potential mechanism in the efficacy of this medium in controlling development of malodors.

Example 11

In this experiment the efficacy of micronized particle N-halamine coated zeolite on inhibition of a common odor-generating enzyme was determined. A solution containing *Canavalia ensiformis* Urease (10 U/mL), 200 mM phosphate buffer, pH 7.0 was incubated with 100 mg of the coated zeolite and control uncoated medium at room temperature. After 5 minutes, the samples were centrifuged for 60 seconds at 10,000 rpm, and the supernatant was removed and urea (15 mM) was added. 100 µL of this solution was assayed following the Sigma Aldrich (St. Louis, Mo.) Ammonia Assay Kit protocol (AA0100). Briefly, a 100 µL aliquot was added to the Ammonia Assay Reagent and incubated for five minutes. Then, 10 µL of L-glutamate dehydrogenase was added and the initial absorbance at 340 nm was recorded. The final absorbance was measured after 5 minutes.

Jack Bean Urease activity was used as an indicator of inhibitory effects. Urease activity alone produced 297.3 µg/mL of NH3, while the negative zeolite control reduced the activity to 158.5 µg/mL. A large decrease in Urease activity occurred with the N-halamine-coated zeolite sample with only 4.5 mcg of ammonia being generated after contact. The result with this medium indicates that the coated granules may exert useful effects on malodor control through inhibition of microbial enzymes such as ureases that generate odor from substrates such as urea, and can be expected to inhibit other enzymes such as lyases, for example, that produce malodorous volatile sulfurous compounds from macromolecules and peptides that contain sulfur residues.

Example 12

The purpose of this experiment was to demonstrate that N-halamine coated zeolite granules, prepared by deposition of micronized particles onto the surface of the aluminosilicate substrate, could serve as an effective malodorant removal medium in an air filtration device. The pleated nonwoven membrane filter was removed from a room air filter (Beiang Corp, Beijing, China, Model A8) and replaced with a cassette 8×12×¾ inches filled with ~1 kilogram of N halamine coated zeolite granules. Then, a 10×10 ft enclosed space with limited air exchange was used to create a malodorous atmosphere by spreading 100 grams of an organic fertilizer on the floor of the room overnight. At this point a panel of six people were admitted singly into the room and each allowed to score the degree of malodor. The air filter fitted with the coated zeolite was then installed in the room for 90 minutes, drawing air through the filter at the rate of 800 cubic meters per hour ($m^3$/hour). Then, the observers were asked to return and score the atmosphere post-air filtration. All observers reported a high degree of removal of the offensive odor.

This result illustrates the usefulness of a N-halamine coated medium as a component of an air filtration treatment train in removing complex mixed offensive odors in a confined air space. This result also illustrates the usefulness of a N-halamine coated medium as a component of an air filtration treatment train in removing complex mixed offensive odors in a confined air space.

Example 13

The purpose of this experiment was to demonstrate the efficacy of the N-halamine coated zeolite medium as a component of an air filtration device used to reduce the odor of marijuana plants in a grow operation in Carnation, Wash. In an administration area of 600 sq ft adjacent to a 5000 sq ft grow facility the odor of the marijuana was noticeable to an observer immediately on entry. The air filtration device used in Example 12 was set up in the room with an 8×12×¾ inch cassette containing ~1 kilogram of N-halamine coated zeolite granules. The device was run at maximum flow for 30 minutes. After that time the observer re-entered the space and determined that the distinct odor of the plants had disappeared altogether. This result confirms the utility of the coated zeolite as a means of a specific nuisance odor control (from marijuana, and suspected to be largely terpenes) in a confined space.

Example 14

This experiment was done to illustrate the ammonia control performance of microparticulate N halamine-coated zeolites in comparison to an uncoated commercial horse stall refresher zeolite product (PDZ). In this experiment odor control properties of animal litters were determined using an ammonia test protocol by exposing them to diluted ammonia solution (0.6 weight percent). One hundred and twenty five mL of animal litter was placed into a 1.25 L glass vessel; each vessel was sealed with plastic film. On a daily basis, 1 mL of the ammonia solution was applied onto the animal litter to simulate daily deposits of urine by an animal using the stall bedding product or the coated zeolite medium. After applying the ammonia solution for 5 minutes the ammonia content in the headspace of each carrier vessel was determined using an $NH_3$ test meter. Tests were conducted daily for 3 days without replacement of the litter media.

It was observed (FIG. 3) that the N halamine coated zeolite granules provided superior and faster odor control than PDZ horse stall refresher product. Owing to the noticeable odor abatement and the relatively low chlorine content of the coated zeolites, the active chlorine component is appeared to be primarily functioning as a rapid odor neutralizer/degrader rather than as an odor absorbent. The level of headspace ammonia content detected after 1 day, 2 days, and 3 days is shown below in Table 1.

TABLE 1

| Headspace Ammonia Contest Detected | | | |
|---|---|---|---|
| | 1 Day | 2 Days | 3 Days |
| Treated Zeolite | 0 ppm | 0 ppm | 3 ppm |
| PDZ Horse Stall Refresher | 8 ppm | 17 ppm | 24 ppm |

Figure 3:
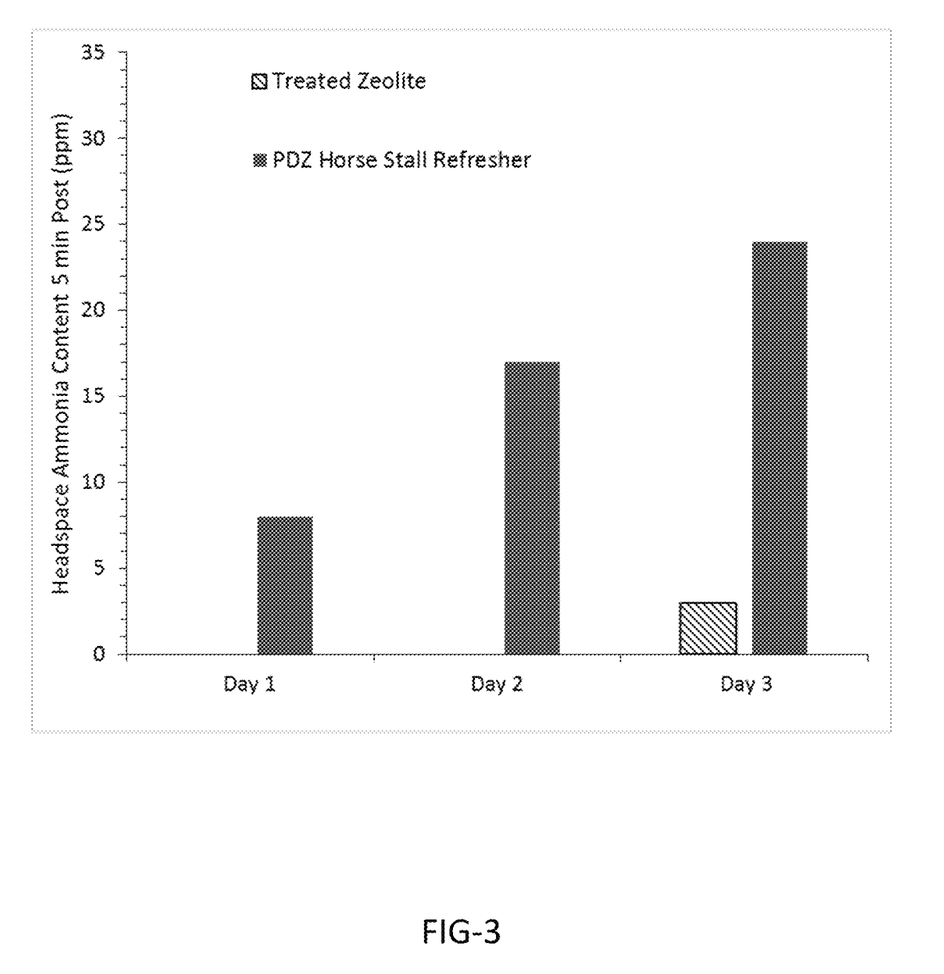
FIG. 3 is a bar graph showing immediate (5 minute) headspace ammonia content after daily litter applications of ammonia equivalent to an aminal's urine deposits, assuming all the urinary urea is microbially converted to ammonia each day as described in Example 14.

FIG. 3 is a bar graph that provides this data. The ammonia contents shown were detected as immediate (5 minute) headspace ammonia content after daily litter applications of ammonia equivalent to an animal's urine deposits, assuming all the urinary urea is microbially converted to ammonia each day.

Example 15

This example illustrates the preparation of a toilet deodorizing spray. One gram of 1,3-dichloro-5,5-dimethylhydantoin and 0.1 gram micronized 1,3-dichloro-2,2,5,5-tetramethylimidazolidin-4-one with were dispersed in 99 grams of vegetable-based ester using magnetic agitation overnight at room temperature. The resulting liquid was clear and without noticeable odor. Chlorine titration indicated the presence of 1875 ppm active chlorine.

Example 16

This example illustrates the preparation of toilet deodorizing spray. One gram of 1-chloro-5,5-dimethylhydantoin and 0.2 gram 1-chloro-2,2,5,5-tetramethylimidazolidin-4-one were dispersed in 30 grams isopropyl myristate using magnetic agitation overnight at room temperature. The resulting liquid was clear and without noticeable odor. Chlorine titration indicated the presence of 489 ppm active chlorine.

Example 17

This experiment was performed to illustrate the odor control performance comparison of a toilet-deodorizing formulation applied as a spray compared with the performance of a commercial product (Poo-pourri "Before-you-go" toilet spray composed of essential oils). Hydrogen sulfide ($H_2S$) was chosen as the surrogate for malodorous volatile compounds emitted by human waste.

Figure 4:
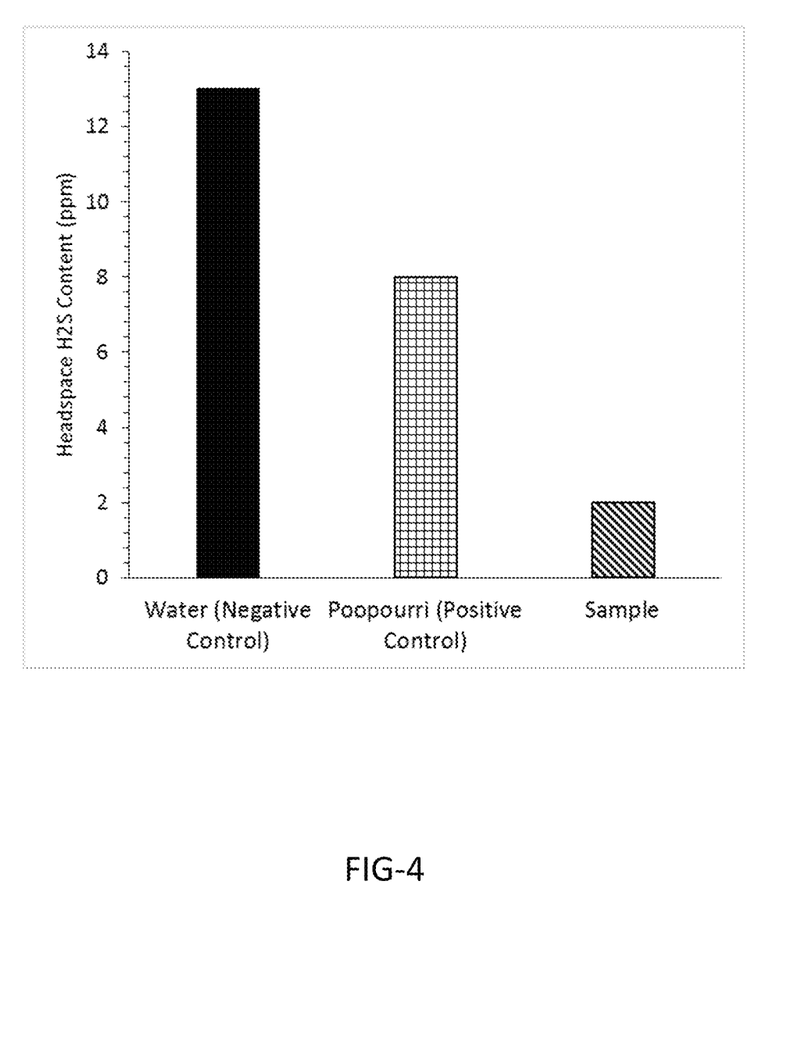
FIG. 4 is a bar graph showing immediate (1 min) headspace content after applying a $H_2S$ solution into the water as described in detail in Example 17.

The odor control properties of the toilet spray formulation were determined by its effects on $H_2S$ solution (lab made) utilizing a hydrogen sulfide ($H_2S$) test protocol: In the procedure used one hundred 100 mL of water was placed into a 1.25 L glass vessel and each vessel was then sealed with plastic film. A negative control vessel received 0.5 mL water as negative control. One half mL of the toilet spray formulation prepared as in example 6, served as test sample, and 0.5 mL of Poo-pourri toilet spray served as positive control. Two mL (2 ml) of the $H_2S$ solution was injected into the water layer in each sealed vessel. After applying the $H_2S$ solution for 1 min, the $H_2S$ content in the headspace of each carrier vessel was determined using the test meter. The results of this experiment are provided in Table 2 and are shown in bar graph form in FIG. 4. The $H_2S$ levels reported were determined immediately (within 1 minute) after applying the $H_2S$ solution into the water.

| Headspace Hydrogen Sulfide (H₂S) Content | |
|---|---|
| Water (Negative Control) | 13 ppm |
| Poopourri (Positive Control) | 8 ppm |
| Experimental Sample | 2 ppm |

It was observed that the N-halamine-coated test sample provided superior and faster odor control than the positive control (Poo-pourri). Owing to the marked effect on $H_2S$ odor abatement and the relatively small amount of active chlorine component in the sample formula, it appeared that the active chlorine was primarily functioning as a rapid $H_2S$ neutralizing/degrading agent rather than as an absorptive agent.

Example 18

The objective of this experiment was to demonstrate that microparticles of functional metal oxides could also be displayed on the surface of zeolite substrate after exposure to dispersions of the particles. In this case suspensions of insoluble micronized cerium oxide particles having an average diameter of 3 microns (Advanced Abrasives Inc) were prepared in water. Exposure of 14×40 mesh zeolite granules to a slurry of CeO led to absorption of the liquid vehicle. Coated granules were then dried and prepared for SEM, and scanning using EDS. These images showed that crystalline microparticles of about 3 microns in size were evenly distributed over the highly irregular surface of the aluminosilicate substrate. Approximately 20% of the elemental composition in a surface linear scan was found to be attributable to oxides of cerium, with signals predominantly over the 4.3-6.3 key range.

This result indicates that surface coating of zeolite with metal oxide preparations known to be functional in a variety of absorptive interactions with water contaminants is achievable with this method. Cerium oxides are known to be highly effective in their interaction with ligands such as fluoride and other toxic contaminants in aqueous medium or in air, especially when Ce is present with other metal oxides such as aluminum and iron.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A garbage bag having walls which are comprised of polyethylene, wherein said walls of the garbage bag are coated with particles of a halogenated heterocyclic N-halamine having a particle size which is within the range of about 0.01 μm to 20 μm, and wherein the particles of the halogenated heterocyclic N-halamine are present only on the surface of the walls of the garbage bag; and wherein the walls of said garbage bag have a wall thickness which is within the range of 0.0002 inch to 0.005 inch thick.

2. The garbage bag of claim 1 wherein the halogenated heterocyclic N-halamine is a partially halogenated hydantoin of the structural formula:

where X1 and X2 independently represent hydrogen atoms or halogen atoms and R1 and R2 independently represent linear or branched alkyl groups containing from 1 to about 10 carbon atoms.

3. The garbage bag of claim 2 wherein the partially halogenated hydantoin is monochloro-5,5-dimethyl hydantoin.

4. The garbage bag of claim 2 wherein $R_1$ and $R_2$ represent an alkyl group containing from 1 to 4 carbon atoms.

5. The garbage bag of claim 2 wherein said halogen atoms are selected from the group consisting of chlorine atoms and bromine atoms.

6. The garbage bag of claim 2 wherein said halogen atoms are chlorine atoms.

7. The garbage bag of claim 2 wherein the partially halogenated hydantoin is selected from the group consisting of $Cl_{0.5-5,5}$-dimethyl hydantoin, $Cl_{0.9-5,5}$-dimethyl hydantoin, $Cl_{1.1-5,5}$-dimethyl hydantoin, $Cl_{1.05-1.4-5,5}$-dimethyl hydantoin, monochloro-5,5-dimethyl hydantoin (MCDMH), $Br_{0.9-5,5}$-dimethyl hydantoin, monobromo-5,5-dimethyl hydantoin (MBDMH), $Cl_{0.5,5}$-methyl-5-ethyl hydantoin, $Cl_{0.9-5}$-methyl-5-ethyl hydantoin, $Cl_{1.1-5}$-methyl-5-ethyl hydantoin, $Ch_{1.05-1.4-5}$-methyl-5-ethyl hydantoin, monochloro-5-methyl-5-ethyl hydantoin, $Br_{0.9-5}$-methyl-5-ethyl hydantoin, and monobromo-5-methyl-5-ethyl hydantoin.

8. The garbage bag of claim 2 wherein the partially halogenated hydantoin is selected from the group consisting of $Cl_{0.9-5,5}$-dimethyl hydantoin, $Cl_{0.9-5}$-methyl-5-ethyl hydantoin, $Cl_{1.1.5,5}$-dimethyl hydantoin, and $Cl_{1.1-5}$-methyl-5-ethyl hydantoin.

9. The garbage bag of claim 1 wherein halogenated heterocyclic N-halamine is selected from the group consisting N-chloro-N-sodiomethylbenzenesulfonamidate trihydrate, N,N-dichloro-4-methylbenzenesulfonamide, N-bromo-N-sodio-4-nitrobenzenesulfonamidate, N,N-dichlorobenzenesulfonamide, N-chloro-N-sodiobenzenesulfonamidate, monochlorosulfamate, dichlorosulfamate, N-chloroimidodisulfonates, sodium N-chloro-N-arylsulfamates, 2,4,6,8-tetrachloro-2,4,6,8-tetrazobicyclooctane-3,7-dione, sodium trichloroimidometaphosphamate, N-halosulfinylamines, N-halo-N-sodioamidates, chloroisocyanurates, N-halocarbamidates, N-halosulfonamidates, N-chloroimidodisulfonate, N,N-dichloromethylamine, 2-chloro-1,3,5-triazine-2,4,6-triamine, 2,4-dichloro-1,3,5-triazine-2,4,6-triamine, 2,4,6-trichloro-1,3,5-triazine-2,4,6-triamine, 1-chloro-5,5-dimethylhydantoin, 1-bromo-5,5-dimethylhydantoin, 1,3-dibromo-5,5-dimethylhydantoin 1-chloro-3-bromo-5,5-dimethylhydantoin, 1,3-dichloro-5,5-dimethylhydantoin, 1-chloro-4,4,5,5-tetramethylimidazolidin-2-one, 1,3-dichloro-4,4,5,5-tetramethylimidazolidin-2-one, 1-chloro-2,2,5,5-tetramethylimidazolidin-4-one, 1,3-dichloro-2,2,5,5-tetramethylimidazolidin-4-one, 1,3-dichloro-s-triazine-2,4,6-trione, trichloroisocyanuric acid, potassium dichloroisocyanurate, sodium dichloroisocyanurate, potassium dibromoisocyanurate, sodium dibromoisocyanurate, mono to hexachloromelamine, mono to hexabromomelamine, 3-chloro-4,4-dimethyl-2-oxazolidinone, N-chlorosuccinimide, 1-chloropyrrolidine-2,5-dione, 1,3-dichlorotetrahydro quinazoline-2,4-dione, 1,4-dichloro-2,2,5,5-tetrasubstitutedpiperazine-3,6-diones, N-chloro-2,2,6,6-tetramethylpiperidine, N-chloro-4-amino-2,2,6,6-tetramethylpiperidine, polymer-bound N-chloro-N-sodiobenzenesulfonamidates, chlorinated polyacrylamide, brominated polyacrylamide, chlorinated poly(methacrylamide), brominated poly(methacrylamide), poly(N-chloro-2,2,6,6-tetramethyl-4-piperidinyl acrylate), poly(N-chloro-hydantoin-methyl-p-styrene) emulsion, 1-chloro-3-bromoalkyltrimethylammonium-4,4,5,5-tetramethyl imidazolidin-2-one, 1-bromo-3-bromoalkyltrimethylammonium-4,4,5,5-tetramethyl imidazolidin-2-one, 1-chloro-3-bromoalkyltrimethylammonium-2,2,5,5-tetramethyl imidazolidin-4-one, 1-bromo-3-bromoalkyltrimethylammonium-2,2,5,5-tetramethyl imidazolidin-4-one, 2-chloro-4-bromoalkyltrimethylammonium-1,3,5-triazine-2,4,6-triamine, 2-bromo-4-bromoalkyltrimethylammonium-1,3,5-triazine-2,4,6-triamine, 1-chloro-3-bromoalkyltrimethylammonium-5,5-dimethylhydantoin, and 1-bromo-3-bromoalkyltrimethylammonium-5,5-dimethylhydantoin.

10. The garbage bag of claim 1 wherein the particle size is within the range of 0.05 µm to 15 µm.

11. The garbage bag of claim 1 wherein the particle size is within the range of 0.1 µm to 12 µm.

12. The garbage bag of claim 1 wherein the particle size is within the range of 0.1 µm to 10 µm.

13. The garbage bag of claim 1 wherein the particle size is within the range of 0.5 µm to 8 µm.

14. The garbage bag of claim 1 wherein the particle size is within the range of 1 µm to 6 µm.

15. The garbage bag of claim 1 wherein the particle size is within the range of 3 µm to 5 µm.

16. The garbage bag of claim 1 wherein the polyethylene is high density polyethylene.

17. The garbage bag of claim 1 wherein the polyethylene is linear low density polyethylene.

18. A garbage bag having walls which are comprised of polyethylene, wherein said walls of the garbage bag are coated with particles of a halogenated heterocyclic N-halamine having a particle size which is within the range of about 0.01 µm to 20 µm, and wherein the particles of the halogenated heterocyclic N-halamine are present only on the surface of the walls of the garbage bag; and wherein the polyethylene is high density polyethylene.

19. A garbage bag having walls which are comprised of polyethylene, wherein said walls of the garbage bag are coated with particles of a halogenated heterocyclic N-halamine having a particle size which is within the range of about 0.01 µm to 20 µm, and wherein the particles of the halogenated heterocyclic N-halamine are present only on the surface of the walls of the garbage bag; and wherein the polyethylene is linear low density polyethylene.

* * * * *